United States Patent [19]
Matsuno et al.

[11] Patent Number: 5,788,628
[45] Date of Patent: Aug. 4, 1998

[54] ENDOSCOPE

[75] Inventors: Shinichi Matsuno; Keiji Ito, both of Tokyo, Japan

[73] Assignee: Asahi Kogaku Kogyo Kabushiki Kaisha, Tokyo, Japan

[21] Appl. No.: 852,797

[22] Filed: May 7, 1997

Related U.S. Application Data

[63] Continuation of Ser. No. 449,680, May 24, 1995, abandoned.

[30] Foreign Application Priority Data

May 26, 1994 [JP] Japan ............................. 6-112399
Nov. 18, 1994 [JP] Japan ............................. 6-284617

[51] Int. Cl.[6] ............................................. A61B 1/04
[52] U.S. Cl. ........................... 600/127; 600/121; 600/125; 600/129
[58] Field of Search .................... 600/121, 123, 600/125, 127, 129, 153, 156, 157, 158, 203, 188, 205, 187

[56] References Cited

U.S. PATENT DOCUMENTS

| | | | |
|---|---|---|---|
| D. 264,494 | 5/1982 | Chapa | D23/40 |
| 4,646,722 | 3/1987 | Silverstein et al. | 128/4 |
| 4,881,810 | 11/1989 | Hasegawa | 128/4 |
| 5,201,908 | 4/1993 | Jones | 128/4 |

FOREIGN PATENT DOCUMENTS 64-6804  2/1989  Japan ............................. 128/4

*Primary Examiner*—Beverly M. Flanagan
*Attorney, Agent, or Firm*—Kane, Dalsimer, Sullivan, Kurucz, Levy, Eisele and Richard, LLP

[57] ABSTRACT

An endoscope includes an endoscope having an elongated insertion portion, a front end body provided on the front end of the elongated insertion portion, and a detachable front end cover which covers said front end body, wherein said front end cover is comprised of a combination of an easily deformable member having a high resiliency and a deformation restricting member having a lower resiliency than the easily deformable member.

17 Claims, 13 Drawing Sheets

ENDOSCOPE

This application is a continuation of application Ser. No. 08/449,680 filed May 24, 1995, now abandoned.

BACKGROUND OF THE INVENTION

1. Field of the Invention

The present invention relates to an endoscope having an end cap which is detachably attached to a front end body of an insertion portion thereof.

2. Description of Related Art

For example, in a known side view type endoscope, a cylindrical front end cover (front end cap) is attached to a front end body formed at a front end of an insertion portion to be inserted in a cavity of a human body. The end cover is usually made of a resilient material, such as a resilient rubber, etc., so that the end cover can be detachably attached to the front end body due. If the thickness (or stiffness) of the end cover is decreased to reduce the diameter thereof, the strength of the end cover becomes too small to hold the substantial shape thereof during attachment to the front end body. To solve this problem, i.e., to ensure that the end cover has a sufficient strength (stiffness), it is also known to form the end cover of a relatively hard synthetic resin material whose elasticity is lower than rubber.

To prevent an accidental detachment of the end cover from the front end body, the end cover is provided on the inner peripheral surface thereof with a flange (peripheral projection) and the front end body is provided on the outer peripheral surface thereof with a circular (peripheral) groove in which the flange can be fitted.

In such a known detachment preventing means, the diameter of the inner peripheral flange is substantially identical to the diameter of the bottom surface of the peripheral groove formed on the outer peripheral surface of the front end body, but is smaller than the diameter of the outer peripheral surface of the remaining portion of the front end body. Consequently, upon attachment of the end cover to the front end body, the end cap is elastically deformed to radially expand the inner flange so as to slide on the outer peripheral surface of the front end body until the inner flange reaches the peripheral groove. As soon as the peripheral flange of the end cover is fitted in the peripheral groove of the front end body, the end cover is returned to the original state to reduce the diameter of the elastically expanded peripheral flange, due to the elastic restoring force. Specifically, repeated elastic deformations occur every time the end cover is attached to or detached from the front end body. Consequently, if the end cover is made of a relatively weak resilient material, eventually, an elastic deformation of the end cover beyond the elastic limit thereof takes place, thus leading to a breakage of the end cover.

SUMMARY OF THE INVENTION

The primary object of the present invention is to provide an endoscope having an end cap which can be easily attached to and detached from a front end body of an insertion portion of the endoscope, wherein little or no breakage of the end cap occurs.

To achieve the object mentioned above, according to the present invention, there is provided an endoscope having an elongated insertion portion, a front end body provided on the front end of the elongated insertion portion, and a detachable front end cap which covers said front end body, wherein said front end cap is comprised of a combination of an easily deformable member having a high resiliency and a deformation restricting member having a lower resiliency than the easily deformable member.

According to another aspect of the present invention, there is provided an endoscope in which a front end body provided on the front end of an elongated insertion portion, and a detachable front end cap which covers said front end body, wherein said front end cap is comprised of a cover portion which covers the front end body and an engaging portion which engages with the front end body, and wherein said engaging portion is made of an easily deformable member having a high resiliency, and said cover portion being made of a deformation restricting member having a lower resiliency than the easily deformable member.

Preferably, the front end body is provided, on the front end of the insertion portion, with a view window, and the front end cap is provided with an opening corresponding to the view window, so that the view window can be exposed to the outside through the opening.

Preferably, the front end body is provided on the front end portion thereof with an air supply passage and a water supply passage, and the front end cap is integrally provided with a nozzle portion oriented toward the view window and connected to the air supply passage and the water supply passage when the front end cap is attached to the front end body.

The front end body and the front end cap can be both cylindrical.

The front end cap can be provided on the outer peripheral surface thereof with at least one engaging recess which can be engaged by a tool which is used to remove the front end cap from the front end body.

The front end cap can be provided on the inner peripheral surface thereof with an engaging projection corresponding to the engaging recess and extending in the axial direction, and the front end body can be provided with an axially extending engaging groove in which the engaging projection of the front end cap can be engaged when the front end cap is attached to the front end body.

The front end body is preferably provided, on the side surface thereof, with a view window, and the front end cap is preferably provided with an opening corresponding to the view window, so that the view window can be exposed to the outside through the opening.

In an embodiment, the front end body is provided with an air supply passage and a water supply passage, both opening toward the view window, and the front end cap is integrally provided with a nozzle portion connected to the air supply passage and the water supply passage when the front end cap is attached to the front end body.

Another object of the present invention is to provide an endoscope having an end cap which can be easily and correctly attached to and detached from a front end body of the endoscope, and particularly a side view type endoscope.

To achieve the object mentioned above, according to the present invention, there is provided an endoscope comprising a front end body provided on a front end of an elongated insertion portion, a detachable front end cap which is detachably attached to the front end body to cover the front end body, and a view window which is provided on the side surface of the insertion portion and which can be exposed to the outside from the front end cap, wherein a substantial part of the front end cap is made of an easily deformable member having a high resiliency, said easily deformable member being supported, at least at the portion thereof that engages with the front end body, by a deformation restricting member having a lower resiliency than the easily deformable member.

In this aspect, the front end body is provided with an air supply passage and a water supply passage, both opening toward the view window, and wherein said front end cap is integrally provided with a nozzle portion connected to the air supply passage and the water supply passage when the front end cap is attached to the front end body.

The front end cap and the deformation restricting member of the front end cap are preferably cylindrical. The front end cap is provided, on the portion thereof corresponding to the engaging portion of the front end cap, with at least one slit which enables the front end cap to elastically deform when the front end cap is attached to the front end body.

The present disclosure relates to subject matter contained in Japanese patent application Nos. 6-112399 (filed on May 26, 1994) and 6-284617 (filed on Nov. 18, 1994) which are expressly incorporated herein by reference in their entireties.

BRIEF DESCRIPTION OF THE DRAWINGS

The invention will be described below in detail with reference to the accompanying drawings, in which.

DESCRIPTION OF THE PREFERRED EMBODIMENT

Figure 1:
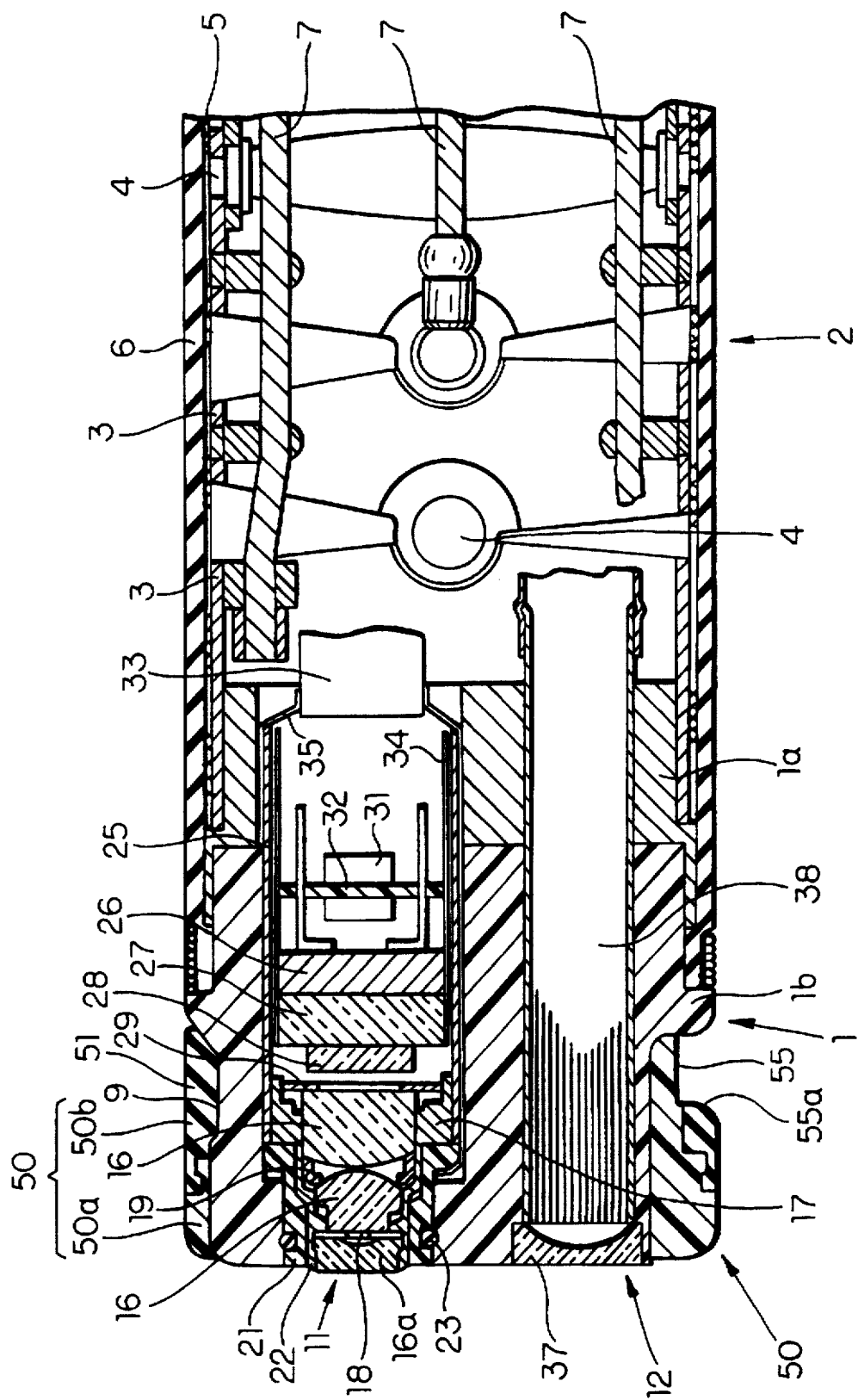
FIG. 1 is a sectional side view of a front end portion of a front view type endoscope having an end cap attached thereto, taken along the line A-B-C-D-E-F-G in FIG. 2, according to the present invention.

The illustrated in FIG. 1 is applied to a front view type endoscope through which an object located axially in front thereof can be viewed. As can be seen in FIG. 1, the front view type endoscope is provided on the front end portion thereof with a front end body 1 which is connected to a front end of a flexible portion 2 provided at the front end of the insertion portion made of an elongated flexible tube that can be bent through a remote control.

The flexible portion 2 consists of a number of ring elements 3 that are rotatably connected by rivets 4 and covered by an inner tubular net 5 and an outer rubber tube 6. The front end of the flexible portion 2 (rubber tube 6) is secured to the outer surface of the front end body 1. An operation wire 7 is provided within the flexible portion 2.

The front end body 1 is comprised of a metal block portion 1a made of stainless steel which is connected to the front end of the flexible portion 2 to be surrounded thereby, and an externally exposed plastic block portion 1b which is connected to the front end of the metal block portion 1a. The front end body 1 is provided on the front end thereof with a view window 11, an illumination window 12, a forceps channel outlet 13, and an air/water injection nozzle 14.

As shown in FIG. 1, there is an objective optical system 16 which is held by a metal lens barrel 17 and located behind the view window 11. The first lens 16a of the objective optical system 16 is caulked and secured to the lens barrel 17 at an intermediate stepped portion of the first lens 16a. An aperture (stop or diaphragm) is provided behind the first lens 16a and a spacer is provided within the lens system 16.

The lens barrel 17 is provided, on the outer peripheral surface of a front half portion thereof, with an insulation ring 21 made of an electrically insulating plastic material. A recess 22 which is formed at the front end portion of the lens barrel 17 is filled with a formless epoxy adhesive, so that the front end of the lens barrel 17 is not exposed to the outside. The insulation ring 21 is fitted in a hole formed in the plastic block portion 1b of the front end body 1 through a sealing O-ring 23.

The lens barrel 17 is provided, on the outer peripheral surface of the rear end portion thereof, with a metal shield pipe 25 fitted and secured thereto. A solid state image pickup device 26 (i.e., a charge coupled device (CCD)) is provided within the shield pipe 25. The light receiving surface of the CCD 26 faces in the direction of the view window 11. A transparent glass cover 27 is connected to the front end of the CCD 26 and a YAG laser filter 28 is adhered to the front end of the glass cover 27. An object image to be viewed is formed on the light receiving surface of the CCD 26 by the objective optical system 16 through the transparent members 27 and 28. A light intercepting mask 29 is provided between the optical system 16 and transparent members 27 and 28.

A printed circuit board 32 which is provided behind the CCD 26 in the shield pipe 25 is provided thereon with an electronic component 31 (e.g. microprocessor etc.) to process image signals supplied from the CCD 26. The PC board 32 is connected to an operating portion (not shown) through a signal cable 33 which extends from the PC board 32 proximally, away from window 11.

Insulation tapes 34 and 35 are wound about the outer peripheral surfaces of the elements within the shield pipe 25 to insulate the inside elements of the shield pipe 25 from the outside of the shield pipe 25. The rear end of the insulation tape 35 of the shield pipe 25 extends to the outer peripheral surface of the front end of the signal cable 33.

Concave lenses 37 are fitted in the illumination windows 12 to widen the orientation angle of illuminating light incident thereto. The emission ends of bundles of light guiding fibers (optical fibers) 38 inserted in the insertion portion of the endoscope are located behind the corresponding concave lenses 37.

A front end cap 50 is detachably attached to the front end of the front end body 1. Specifically, the end cap 50 is fitted on the outer periphery of the plastic block portion 1b of the front end body 1 from the front side. The end cap 50 can be detached from the front end body 1, using an end cover removing tool 100 (FIG. 3), as will be discussed hereinafter.

The end cap 50 has a generally cylindrical shape whose diameter is substantially identical to the outer diameter of the front end body 1. The end cap 50 has an open rear end and a front end which is provided with the air/water injection nozzle 14 formed thereon. The edges of the end cap 50 are all smoothly rounded so as not to injure the mucous membranes of a body cavity of a patient.

Figure 2:
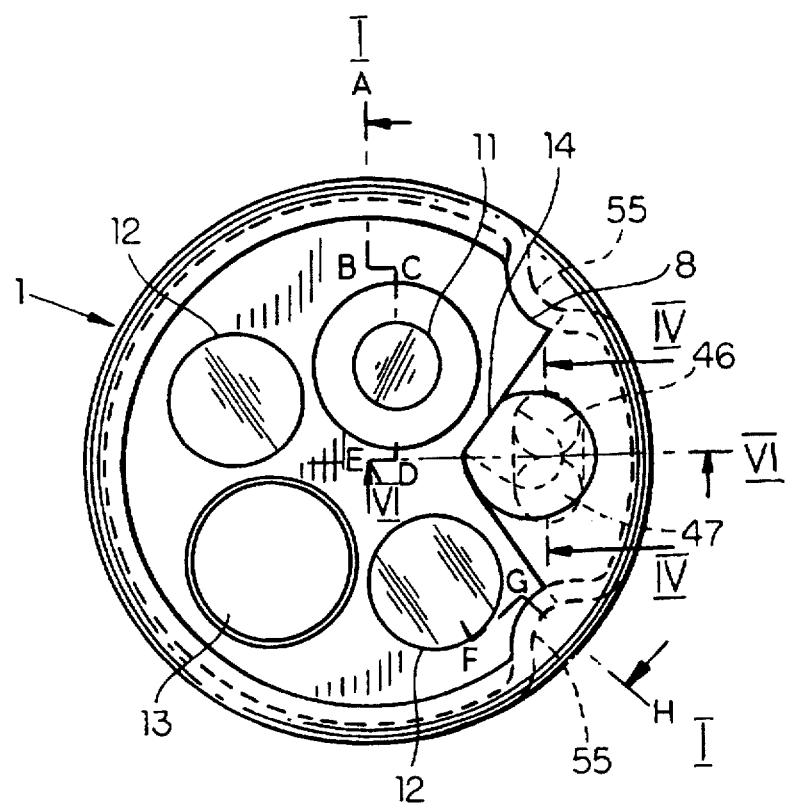
FIG. 2 is a front elevational view of a front end portion of a front view type endoscope having an end cap attached thereto, shown in FIG. 1.
Figure 4:
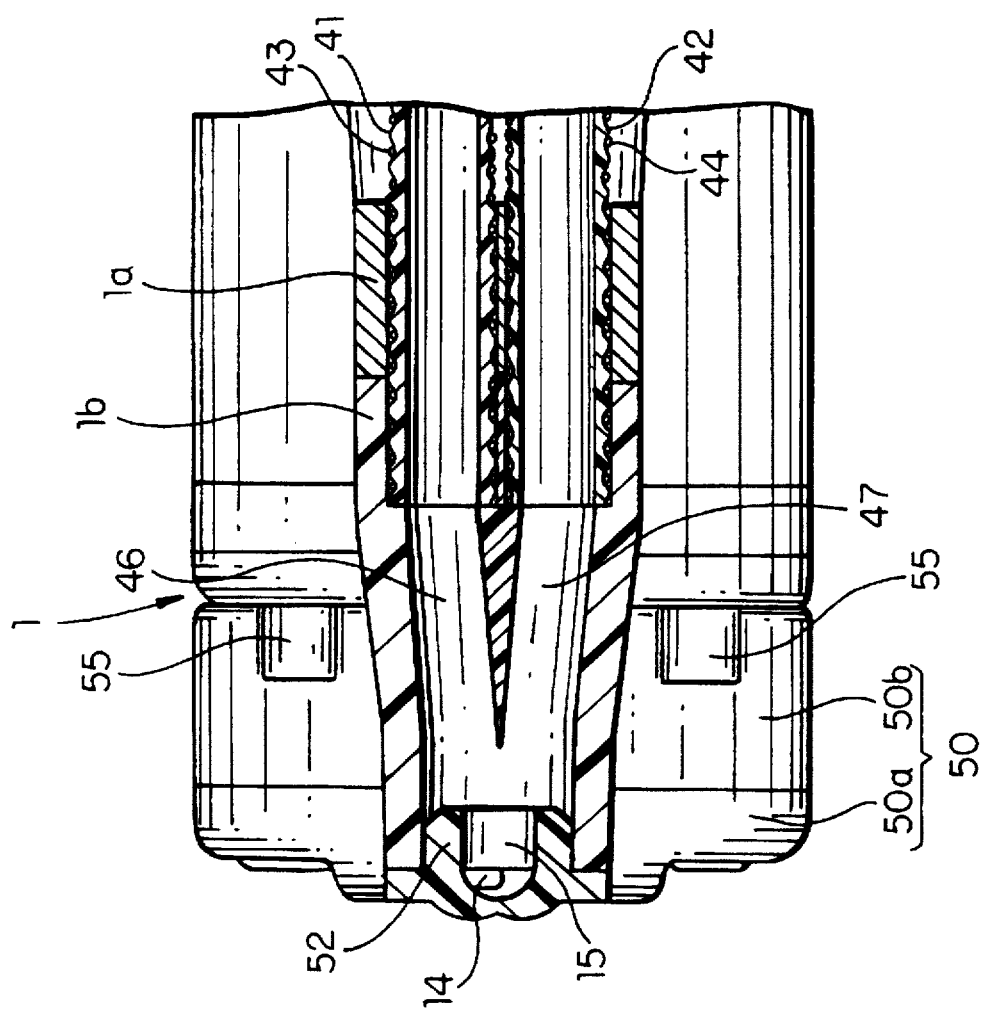
FIG. 4 is a sectional view of a front end portion of a front view type endoscope having an end cap attached thereto, taken along the line I-J in FIG. 2.

In FIG. 4 which shows a sectional view taken along the line I-J in FIG. 2, an air supply tube 41 and a water supply tube 42, both provided in the insertion portion of the endoscope are inserted in and secured to axial holes formed in the front end body 1 to extend in the axial direction of the front end body 1. The tubes 41 and 42 are made of an ethylene tetrafluoride resin and are provided on the outer peripheral surface thereof with helical grooves located within the flexible portion 2, so that thin spring wires 43 and 44 are helically fitted in the helical grooves so as to prevent a buckling of the tubes.

Figure 5:
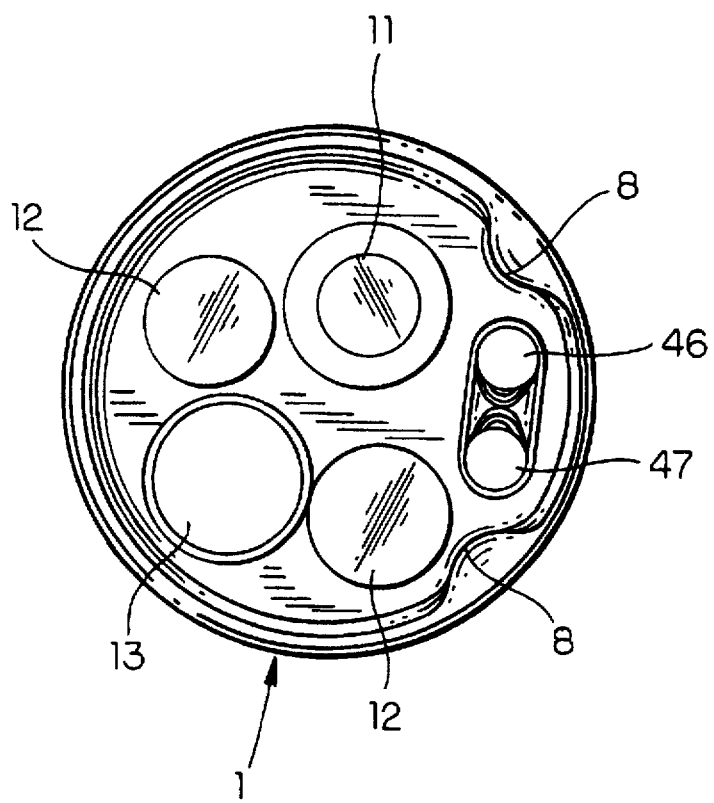
FIG. 5 is a front elevational view of a front end portion of a front view type endoscope, having a removed end cap, according to the present invention.

An air supply hole 46 and a water supply hole 47 formed in the front end body 1 and connected to the corresponding air supply tube 41 and water supply tube 42 are connected at the terminal ends thereof to a common passage 15 (in FIG. 4) which opens into the end surface of the front end body 1 as an oval opening, as can be seen in FIG. 5 which shows a front elevational view of the front end body 1 with the removed end cap 50.

Figure 6:
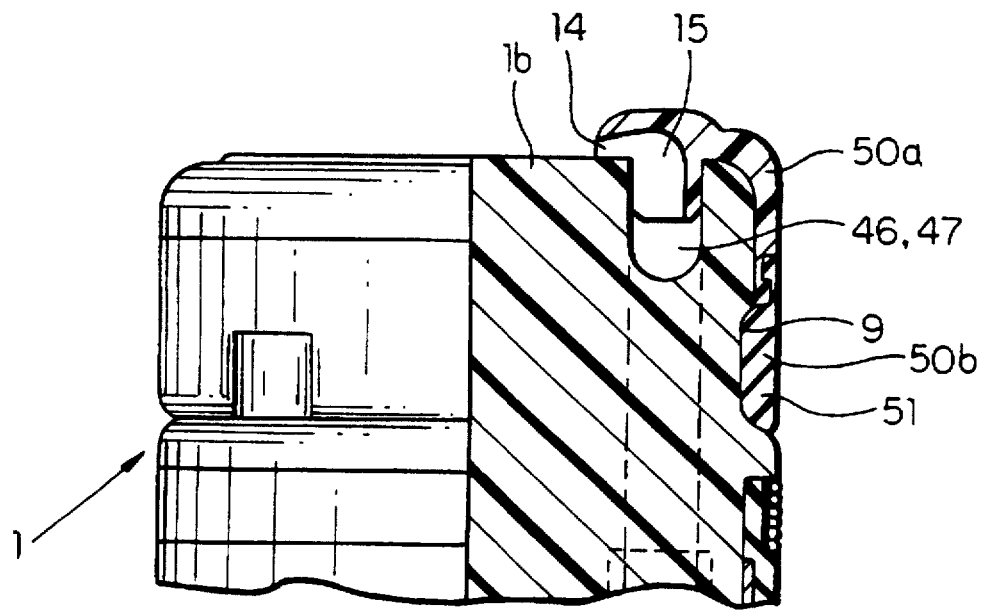
FIG. 6 is a side sectional view of a front end portion of a front view type endoscope having an end cap attached thereto, taken along the line E-K in FIG. 2.

The air/water injection nozzle 14 of the end cap 50 opens into the front end surface of the end cap 50, and is connected to an air/water supply passage 15 which is formed in the end cap 50 to connect the air supply hole 46 and the water supply hole 47 to the air/water injection nozzle 14, as shown in FIG. 6. It should be noted that the end cap 50 is provided with a proximally extending projection 52 which defines therein the air/water supply passage 15 and which is inserted in the corresponding hole of the front end body 1, as shown in FIG. 4. The projection 52 prevents air or water from leaking.

The air or water which is selectively supplied into the air/water injection nozzle 14 through the air supply tube 41 or the water supply tube 42, so that air or water can be selectively injected from the nozzle 14 toward the outer surface of the view window 11.

Figure 7:
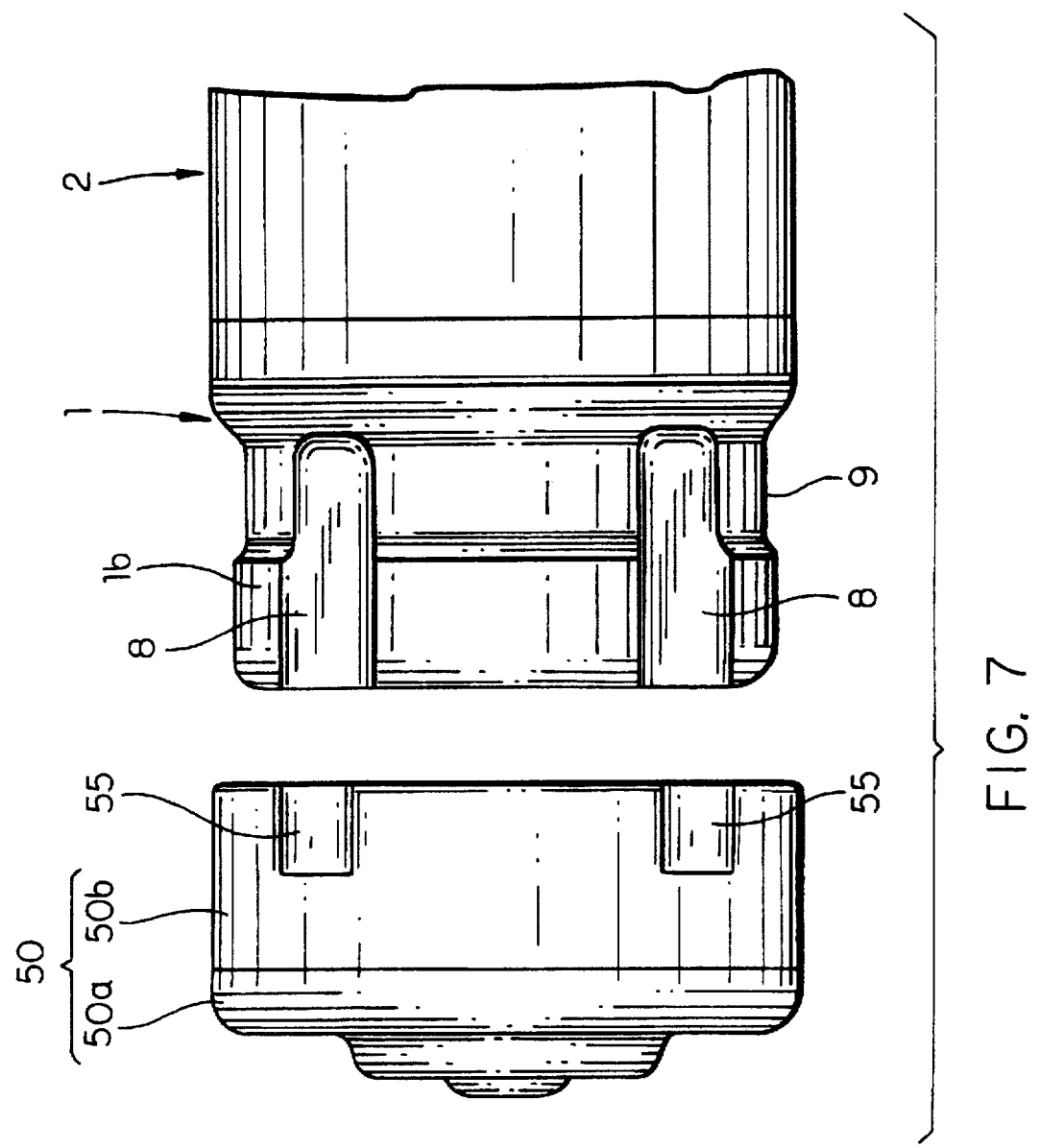
FIG. 7 is a side view of a front end body of a front view type endoscope, and an end cap removed from the front end body, according to the present invention.

As can be seen in FIGS. 1 and 7, the plastic block portion 1b of the front end body 1 is provided on the outer peripheral surface thereof with a peripheral recess (engaging recess) 9, and the end cap 50 is provided on the inner peripheral surface with an inner flange 51 which is shaped such that the inner flange 51 can be fitted in the peripheral recess 9 when the end cap 50 is attached to the front end of the front end body 1.

Figure 8:
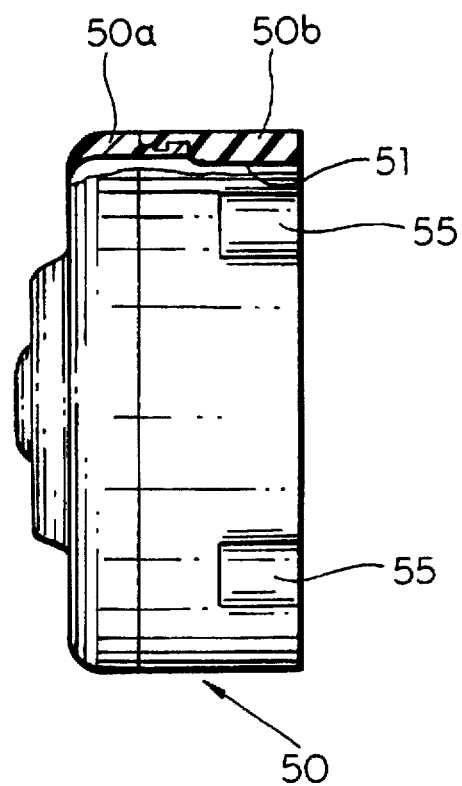
FIG. 8 is a partial sectional side view of an end cap according to the present invention.
Figure 9:
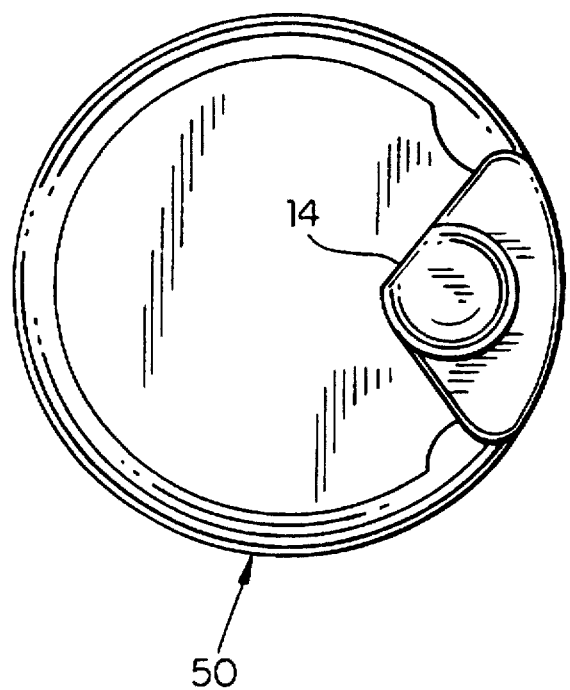
FIG. 9 is a front elevational view of an end cap detached from an front end body of an endoscope, according to the present invention.
Figure 10:
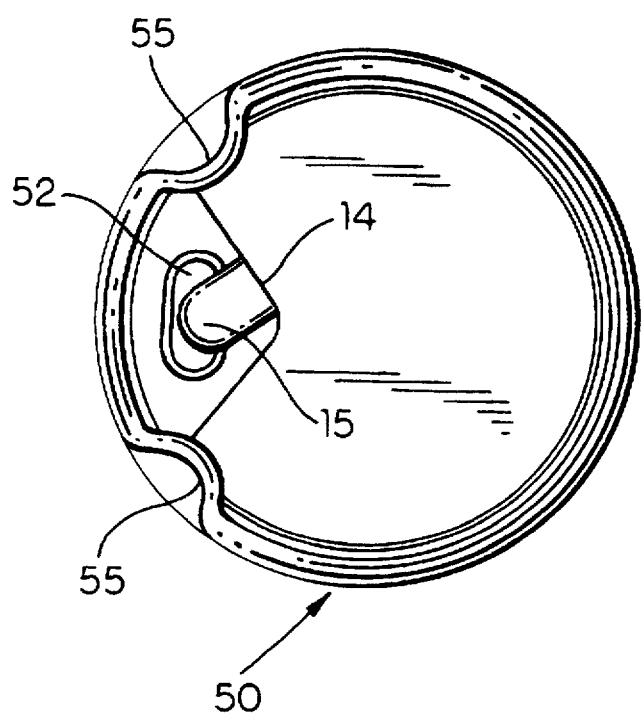
FIG. 10 is a back view of an end cap shown in FIG. 9.

The end cap 50 is comprised of a deformation restricting portion 50a which is formed of a plastic material such as polycarbonate resin having an extremely low resiliency and which is provided on the front portion of the end cap corresponding to the front end of the front end body 1 and a deformation permitting portion 50b which is made of a rubber material such as polyurethane rubber whose resiliency is higher than that of the deformation restricting portion 50a and which is provided on the rear portion of the end cap 50 on which the inner flange 51 is formed, as shown in FIG. 8. FIGS. 9 and 10 show a front view and a back view, respectively, of the end cap 50.

The deformation restricting portion 50a and the deformation permitting portion 50b of the end cap 50 are provided with corresponding hook portions formed in opposite directions, which can be engaged with each other, as can be seen in FIG. 8. Thus, the deformation restricting portion 50a and the deformation permitting portion 50b are firmly interconnected through the engaging hooks to form the end cap 50. Alternatively, it is possible to integrally mold the deformation restricting portion 50a and the deformation permitting portion 50b, using the same molding die.

To attach the end cap 50 to the front end body 1, the deformation permitting portion 50b of the end cap 50 is elastically deformed (expanded) and the inner flange 51 of the end cap 50 is slid on and along the outer surface of the front end body 1, from the front end of the front end body 1.

During the sliding movement, since the deformation restricting portion 50a maintains the original shape so as to ensure the sliding contact with the outer peripheral surface of the front end body 1 without elastically deforming, the end cap 50 can be easily fitted onto the front end body 1.

When the inner flange 51 is fitted into the peripheral recess 9 of the front end body 1 as a result of the sliding movement of the expanded inner flange 51 onto the outer peripheral surface of the front end body 1, the end cap 50 is returned to the original state due to the elastic restoring force, as shown in FIG. 1, so that the end cap 50 can be firmly connected to the front end body 1. In this state, the outer surface of the end cap 50 is substantially flush with the outer peripheral surface of the front end body 1.

The end cap 50 is provided on the outer peripheral surface of the rear portion thereof with a pair of recesses 55 spaced in the circumferential direction. The recesses 55 are of a generally "L"-shape having a rounded connecting corner, as shown in FIG. 2. In the side view shown in FIG. 1, the recesses 55 are provided on the front end thereof with upright walls 55a substantially perpendicular to the outer peripheral surface of the front end body 1. The rear ends of the recesses 55 extend to the rear end of the end cap 50.

The front end body 1 is provided with recesses 8 whose shape corresponds to the shape of the recesses 55 of the end cap 50, which extend from the front end of the front end body 1 in parallel with the axis of the end cap 50 so as to prevent the recesses 55 from interfering with the front end body 1 upon attachment of the end cap 50 to the front end body 1, as shown in FIGS. 5 and 7.

There is no recess 55 on the front portion of the end cap 50. Alternatively, the front portion of the end cap 50 is provided on the inner peripheral surface thereof with projections which can be fitted in the recesses 8 of the front end body 1 and which have the same cross-sectional shape as the recesses 55. The projections begin with the intermediate inner surface portion of the end cap 50 at which the recesses 55 begin on the outer surface portion of the end cap 50.

Thus, upon attachment of the end cap 50 to the front end body 1, the positioning can be carried out by registering the recesses 55 with the recesses 8. Once the end cap 50 is attached to the front end body 1, the inner projections of the end cap 50 are fitted in the corresponding recesses 8 of the front end body 1, so that no relative rotation between the end cap 50 and the front end body 1 occurs.

Figure 3:
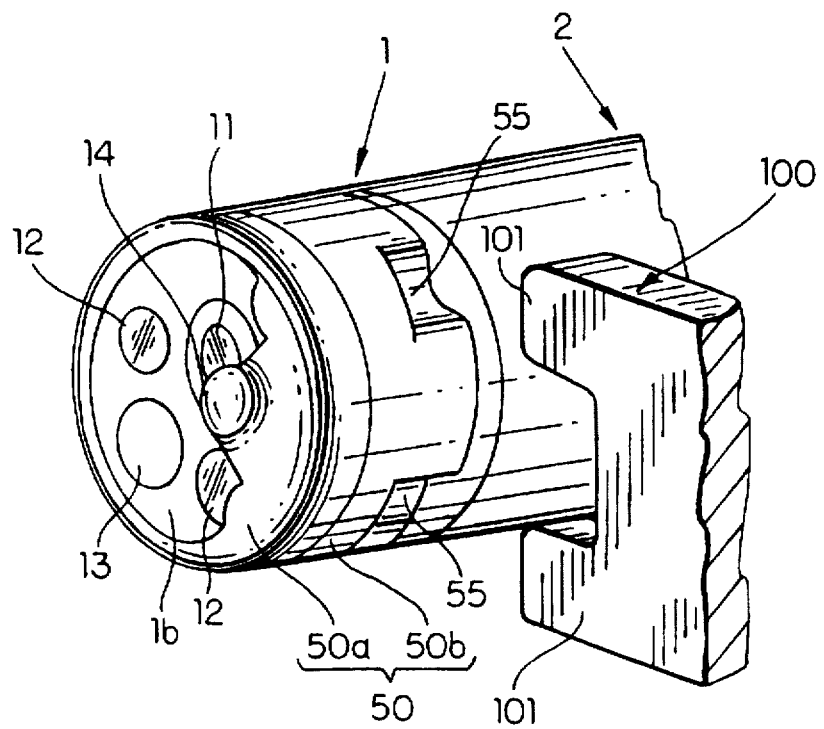
FIG. 3 is a perspective view of an end cap removing tool and a front end portion of a front view type endoscope, shown in FIG. 1.

The end cap removing tool 100 has bifurcated arms 101 which can be fitted in the corresponding recesses 55 of the end cap 50 to remove or detach the end cap 50 from the front end body 1, as shown in FIG. 3. The tool 100 is made of a metal or hard plastic material. The projecting arms 101 of the tool 100 are spaced to correspond to the recesses 55 of the end cap 50.

To detach the end cap 50 from the front end body 1, the projecting arms 101 of the tool 100 are engaged in the corresponding recesses 55 of the end cap 50, and thereafter, the rear portion of the front end body 1 is held and pulled rearwardly by an operator's fingers. Consequently, the rearward movement of the front end body 1 takes place without moving the end cap 50 which is held by the operator's fingers, and hence, the end cap 50 can be detached from the front end body 1. During the detachment of the end cap 50, the inner flange 51 of the deformation permitting portion 50b of the end cap 50 is elastically expanded to ride over the outer peripheral surface of the front end body 1. Consequently, the detachment can be easily carried out.

The electronic image transfer means using the solid state image pickup device (CCD) 26 can be replaced with an optical image transfer means using a bundle of image guiding fibers (optical fibers). Furthermore, the present invention can be applied to a hard-endoscope.

As can be understood from the above discussion, according to the present invention, the end cap 50 is provided with a deformation restricting portion which is made of an extremely low resilient material to maintain the shape of the end cap 50 during the attachment or detachment of the end cap 50, and a deformation permitting portion (engaging portion) which is made of a resilient material which is adapted to prevent the end cap 50 from being accidentally detached from the front end body 1 of the endoscope. Consequently, upon attachment or detachment of the end cap, the elastic deformation of the engaging portion easily occurs while maintaining the cross-sectional shape of the end cap 50 with the help of the deformation restricting portion during the attachment or detachment of the end cap 50 to or from the front end body 1. Thus, the end cap 50 can be easily attached or detached from the front end body 1 of the endoscope without being broken.

An improved side view type endoscope according to a second embodiment of the present invention will be discussed below with reference to FIGS. 11 through 15.

Figure 11:
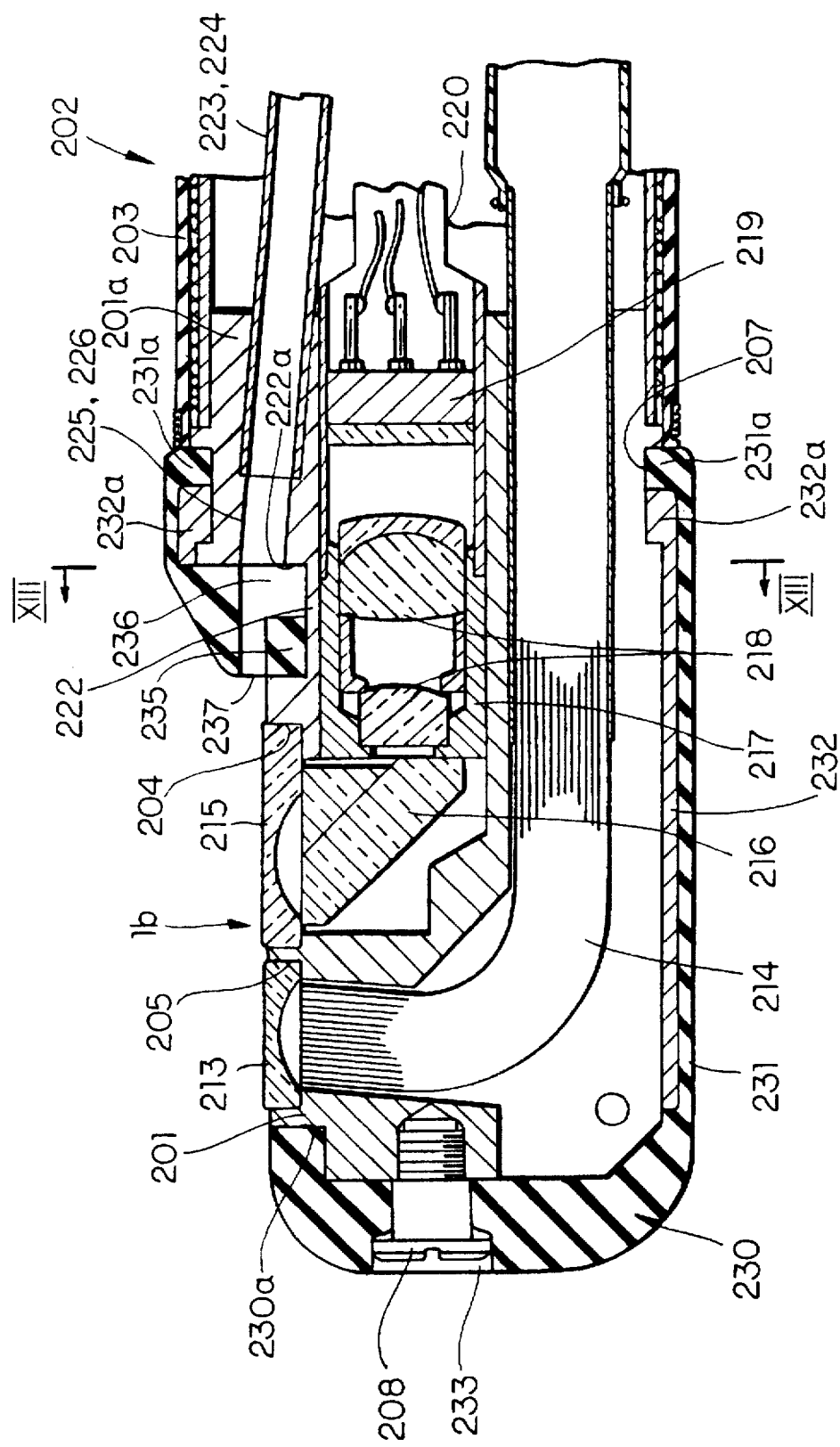
FIG. 11 is a side sectional view of a front end portion of a side view type endoscope having an end cap attached thereto, according to another aspect of the present invention.
Figure 12:
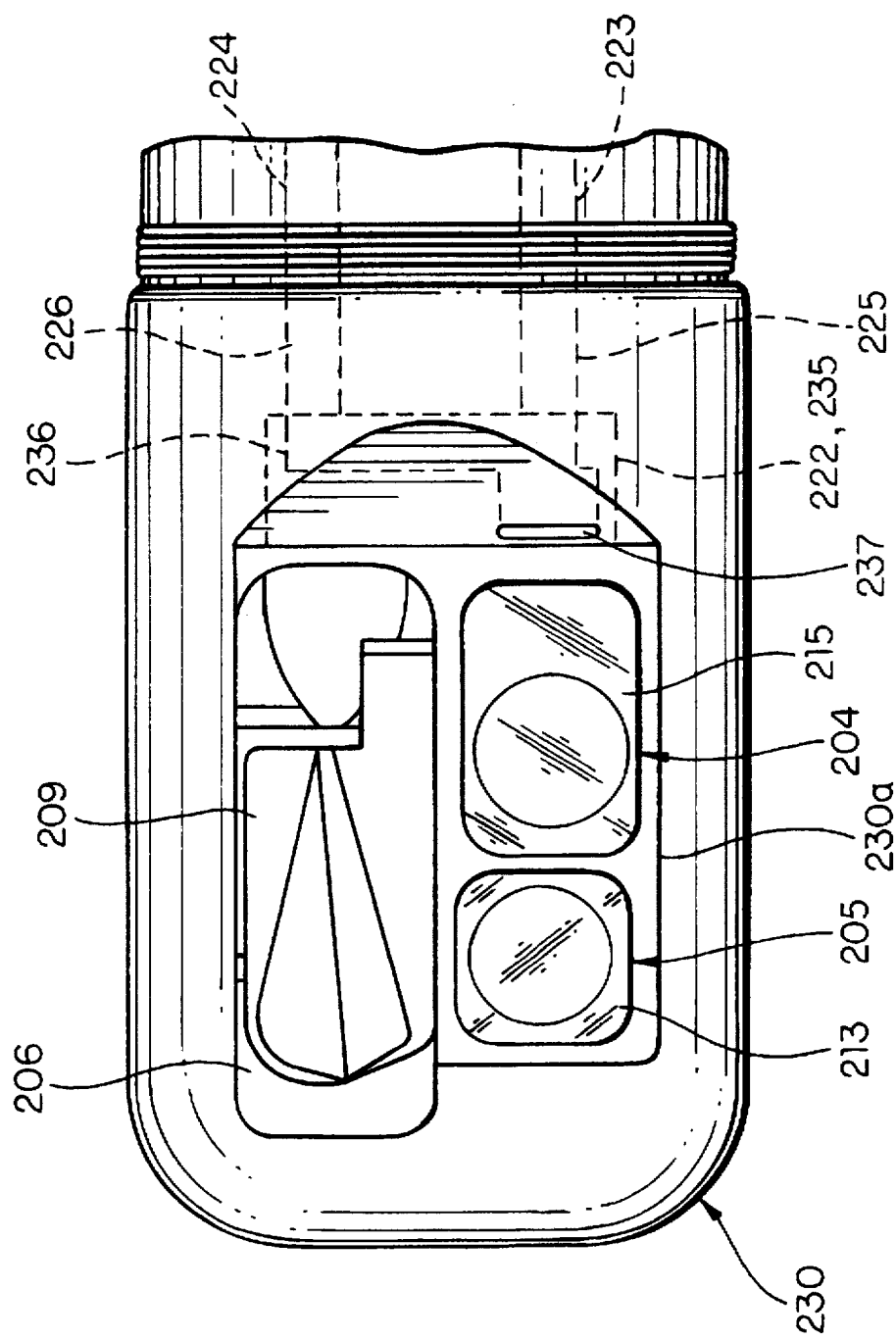
FIG. 12 is a plan view of a front end portion of a side view type endoscope shown in FIG. 11.
Figure 13:
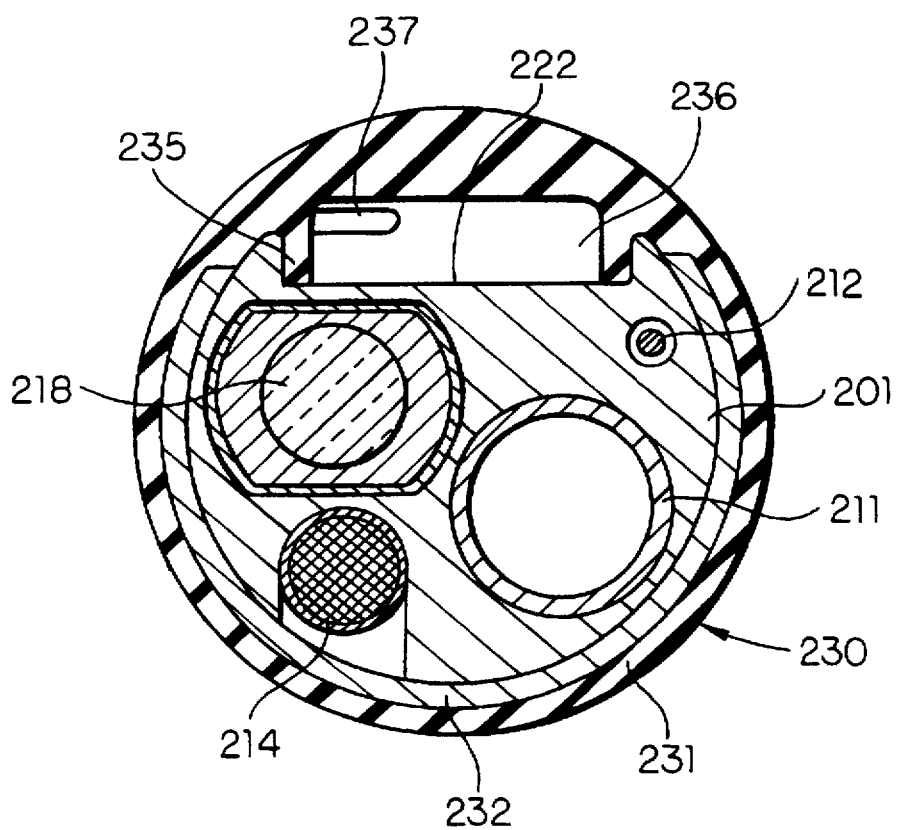
FIG. 13 is a sectional view of a front end portion of a side view type endoscope, taken along the line M—M in FIG. 11.

The front end body 201 of the side view type endoscope is formed of a generally circular metal rod having a partially flat surface portion 1b, as shown in FIGS. 11 and 13. The front end body 201 is provided on the flat surface portion 1b thereof with a view window 204, an illumination window 205, and a treatment tool insertion opening 206 (FIG. 12). The flat surface portion is defined by the remaining circular rod portion (extruding portion) 201a which is located behind (right side of the flat surface portion 1b in FIG. 11) the flat surface portion 1b. The front end body 201 including the extruding portion 201a is fitted in a front opening 202 of a flexible endoscope for attaching the front end body 201 to the front end of the insertion portion of the endoscope which has a structure of an elongated flexible tube. A flexible rubber tube 203 seals the outer periphery of the front opening 202 of the endoscope, as shown in FIG. 11.

As can be seen in FIG. 11, the illumination window 205 is provided with an orientation lens 213 formed of a concave lens fitted and secured therein for diffusing illumination light incident thereto. A bundle of optical fibers (optical fiber bundle) 214 is provided below the orientation lens 213 for transmitting illumination light to the orientation lens 13. The emission end of the fiber bundle 214 is opposed to the orientation lens 213.

The view window 204 is provided with a cover lens 215 for a viewing optical system secured thereto. The front end body 201 includes a prism 216 located below the cover lens 215 to deflect the optical axis of the viewing optical system by 90 degrees, an objective lens 218 and a solid state image pickup device 219. The objective lens 218 and the solid state image pickup device 219 are provided in a lens barrel 217. The solid state image pickup device 219 (e.g., a charge coupled device (CCD)) and has a light receiving surface located at an image forming position in which an object image is formed by the objective lens 218. The CCD 219 is connected to an operating portion (not shown) through a signal cable 220 which extends rearward within the endoscope.

The front end body 201 is provided with a recessed groove 222 having a flat bottom surface, located behind the cover lens 215, as shown in FIGS. 11, 12 and 13. The groove 222 has a lateral width substantially identical to the width of the flat surface portion 1b of the front end body 201 and a predetermined length in the longitudinal direction of the endoscope.

The recessed groove 222 is defined by a vertical rear end wall 222a which is provided with an air supply passage 225 and a water supply passage 226. The air supply passage 225 and the water supply passage 226, both of which open into the recessed groove 222 are connected to an air supply pipe 223 and a water supply pipe 224, respectively.

Figure 14:
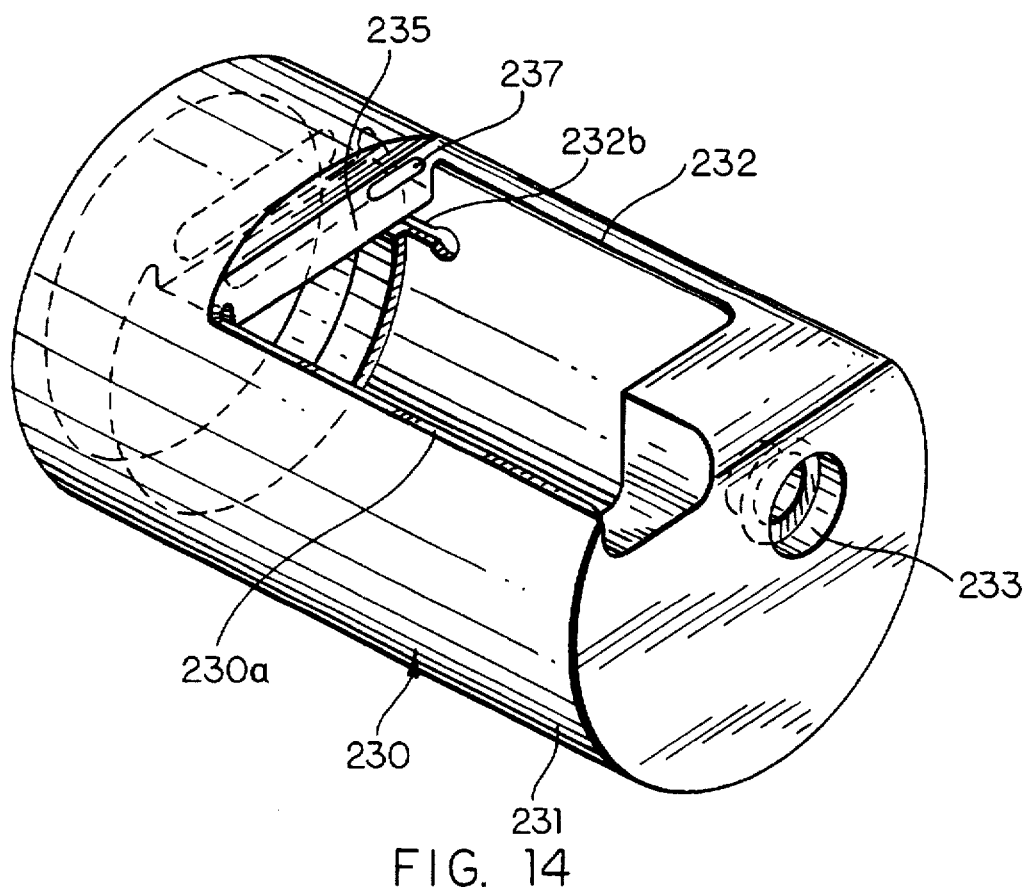
FIG. 14 is a perspective view of an end cap to be attached to a front end of a side view type endoscope, shown in FIG. 11.

The portion of the front end body 201 other than the view window 204, the illumination window 205, and the treatment tool insertion opening 206 is entirely covered by a front end cap 230 which is formed of a water-tight resilient material, such as resilient fluororubber. The front end cap 230 is in the form of a cap having a closed front end and an open rear end. The front end cap 230 is provided with an opening 230a corresponding to the view window 204, the illumination window 205, and the treatment tool insertion opening 206, as shown in FIG. 14.

Figure 15:
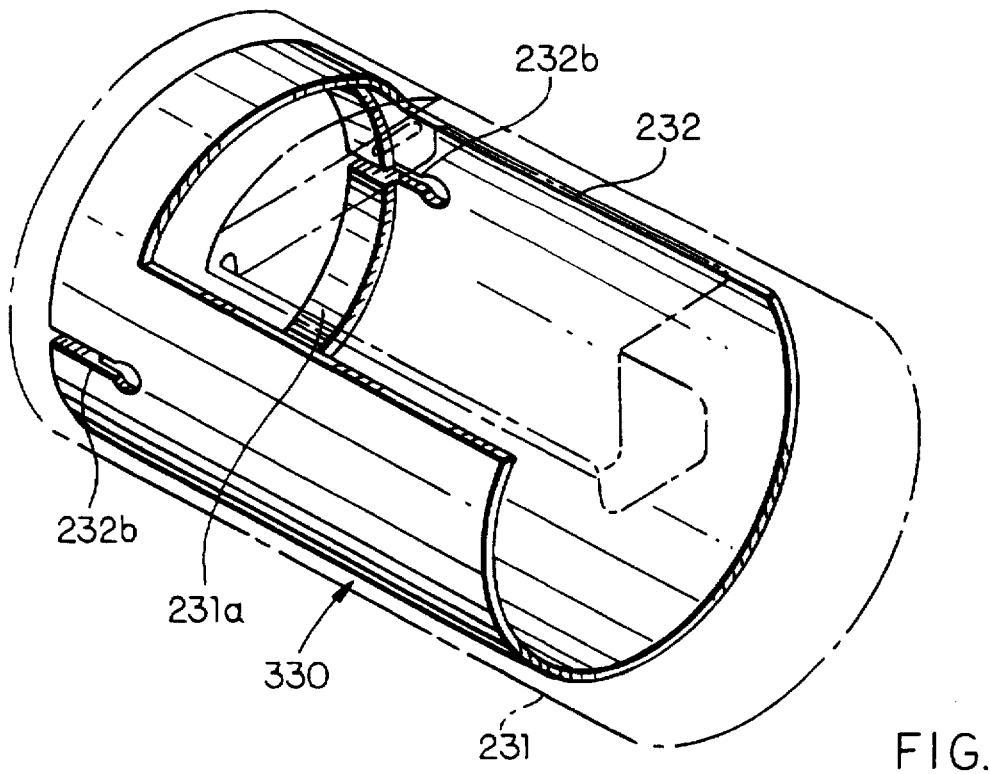
FIG. 15 is a partially sectioned side view of a front end portion of a side view type endoscope having a removed end cap, according to the present invention.

The end cap 230 is comprised of a cover body (main body) 231 formed of a resilient material such as fluororubber and a cover frame 232 which is provided on the inner surface of the cover body 231 to restrict the deformation of the cover body 231. Specifically, the cover frame 232 is provided only on the portion of the inner surface of the main body 231 that would otherwise contact with the inner surface of the front end body 201. As can be seen in FIG. 15, the cover frame 232 is in the form of a ring at the rear end thereof (left end in FIG. 15), and the remaining portion of the cover frame 232 is generally "C"-shaped to define an upper opening corresponding to the view window 204, etc.

The material of the cover frame 232 is not formed of a material having resiliency like rubber, but instead the cover frame 232 is formed of a metal or plastic to exhibit a slight elastic deformability. The main body 231 is aligned with the cover frame 232 integrally adhered thereto.

The main body 231 and the cover frame 232 of the end cap 230 are provided on the rear ends thereof with inner peripheral flanges (low projections) 231a and 232a that are fitted in the peripheral groove 207 formed on the front end body 201 to prevent the end cap 230 from being accidentally disengaged from the front end body 201 when the end cap 230 is attached to the front end body 201.

The cover frame 232 is provided on the annular rear end thereof with a pair of diametrically opposed slits 232b which open at the rear ends. The slits 232b facilitates the attachment of the end cap 230 to the front end body 201. The end cap 230 is provided on the front end thereof with a hole 233 with a spot facing, in which a screw 208 can be inserted. Specifically, the end cap 230 is secured to the front end body 201 by the screw 208 which is screwed in the front end body 201 through the hole 233.

The main body 231 of the end cap 230 is provided with an inwardly projection 235 which can be air-tightly fitted in the peripheral groove 222 of the front end body 201 when the end cap 230 is attached to the front end body 201. The projection 235, when fitted in the recessed groove 222, also serves as a stop to prevent the relative rotation of the end cap 230 with respect to the front end body 201.

The end cap 230 is provided with a connecting groove 236 located behind the projection 235. The connecting groove 236 extends in the radial direction perpendicular to the longitudinal axis of the end cap 230. The connecting groove 236 opens into the air supply passage 225 and the water supply passage 226 when the end cap 230 is attached to the front end body 201.

The nozzle 237 opens into the front end wall of the projecting piece 235 of the main body 231 of the end cap 230 and is directly connected to the connecting groove 236. The nozzle 237 is oriented toward the outer surface of the cover lens 215 when the end cap 230 is attached to the front end body 201. Consequently, air or water supplied from the air supply pipe 223 or the water supply pipe 224 is injected from the nozzle 237 through the connecting groove 236 toward the outer surface of the cover lens 215.

A remote-control treatment tool 209 is provided within the treatment tool insertion opening 206 of the end cap 230. The front end of the treatment tool insertion channel 211 opens toward the insertion opening 206, as shown in FIG. 13. An operation wire 212 is provided within the front end cap 230 so as to swing the treatment tool erecting piece 209 by a remote-control (not shown) during treatment.

When the endoscope as constructed above is used, the cleaned front end cap 230 is attached to the cleaned front end body 201, while expanding the end cap 230. Specifically, upon attachment, the inner peripheral flanges 231a and 232a and the projection 235, etc., are elastically deformed (expanded) due to the elasticity of the end cap 230. When the end cap 230 is securely attached to the front end body 201, the inner peripheral flanges 231a, 232a and the projection 235, etc., are returned to their initial state due to the elastic restoring force, so that the flanges 231a, 232a, and the projection 235 are firmly engaged in the peripheral groove 207 and the recessed groove 222, respectively.

It should be noted that upon deformation, the cover frame 232 prevents the main body 231 from being excessively deformed. Specifically, an adequate deformation of the end cap 230 takes place when the latter is attached to the front end body 201, thereby, ensuring that the end cap 230 is securely attached to the front end body 201. When the end cap 230 is attached to the front end body 201, the inner peripheral flanges 321a and 232a of the end cap 230 are engaged in the peripheral groove 207 of the front end body 201. Thus, the end cap 230 can be firmly secured to the front end body 201 without being accidentally detached therefrom.

Thereafter, the machine screw 208 is inserted in the hole 233 of the end cap 230 and screwed in the threaded hole of the front end body 201 to steadfastly secured connect the end cap 230 to the front end body 201.

In this state, the view window 204, the illumination window 205, and the treatment tool insertion opening 206 are exposed to the outside through the opening 231; the nozzle 237 faces the outer surface of the cover lens 215; and, the air supply passage 225 and the water supply passage 226 are connected to the connecting groove 236.

Since the air and water supply passages between the connecting groove 236 and the outlet port of the nozzle 237 are air-tight and water-tight sealed by the resilient main body 231 with respect to the front end body 201, there is no leakage of air or water therethrough.

To wash or clean the endoscope after the latter is use, the screw 208 is loosened from the hole 233, and thereafter, the end cap 230 is slid on the front end body 201 in the direction opposite to that of the sliding movement of the end cap for the attachment, while expanding the rear end portion of the end cap. Thus, the end cap 230 can be detached or removed from the front end body 201. Thereafter, a brush (not shown) is inserted in the air supply pipe 223 or the water supply pipe 224 through the exposed air supply passage 225 or water supply passage 226 to clean or wash the same. Furthermore, the nozzle 237 formed in the end cap 230 thus detached can be washed or cleaned from the front end side or rear end side thereof.

As can be understood from the above discussion, according to the present invention, since the end cap 230 is comprised of the main body formed of a resilient material and a deformation restricting member which restricts the elastic deformation of the main body, thereby, no excess deformation of the main body occurs upon attachment of the end cap 230 to the front end body 201 of the endoscope. Consequently, an adequate elastic deformation of the main body necessary to attach the end cap 230 to the front end body takes place, so that the end cap 230 can be easily and securely attached to the front end body.

Furthermore, according to the present invention, since the nozzle 237 which is adapted to inject a cleaning fluid toward the outer surface of the view window 204 is formed in the front end cap 230 which is detachably attached to the front end body 201 of the endoscope, the nozzle 237 formed in the front end cap 230 and the fluid supply passages (air/water supply passages 225/225 and air/water supply pipes 223/224) formed in the front end body 201 can be easily and completely cleaned or washed when the front end cap 230 is detached/removed from the front end body after the endoscope is used.

Figure 16:
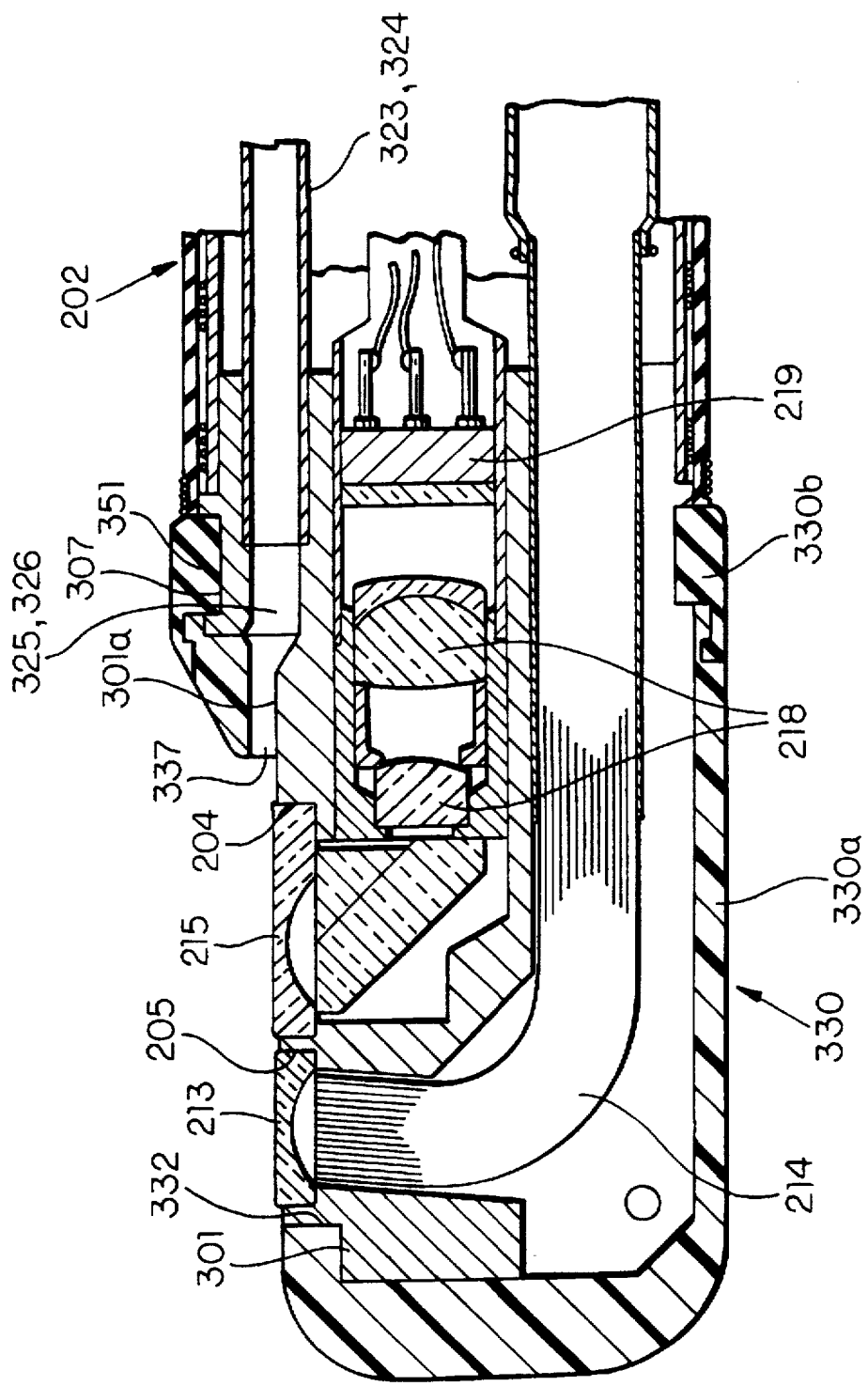
FIG. 16 is a sectional side view of a front end body of a side view type endoscope, according to another aspect of the present invention.
Figure 17:
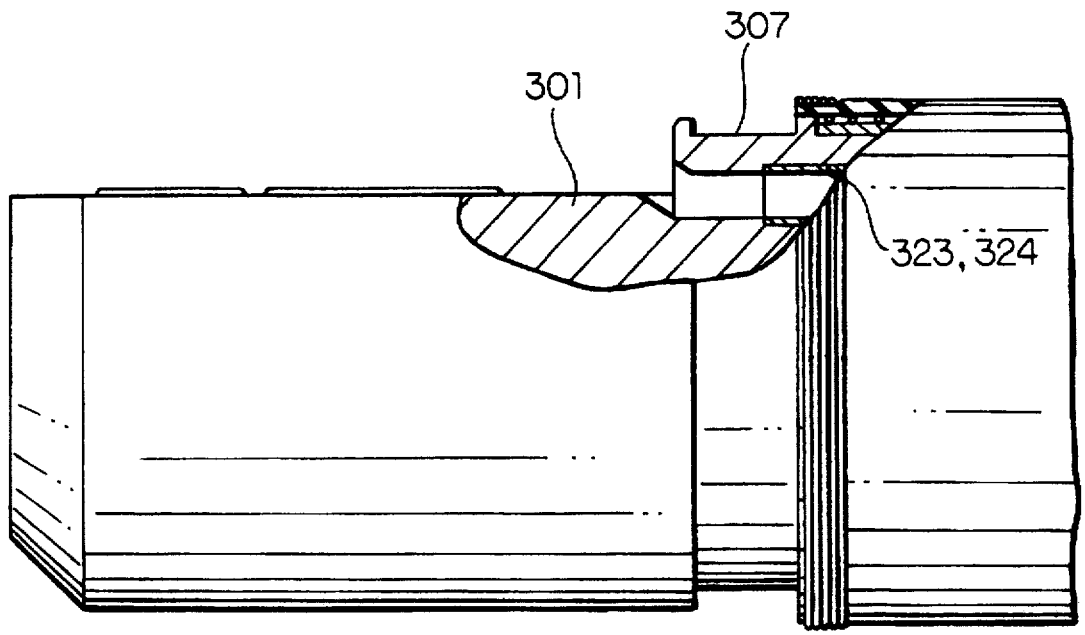
FIG. 17 is a partially sectioned side view of a front end portion of a side view type endoscope having a removed end cap, according to the present invention; and, FIG. 18 is a sectional side view of an end cap, according to the present invention.
Figure 18:
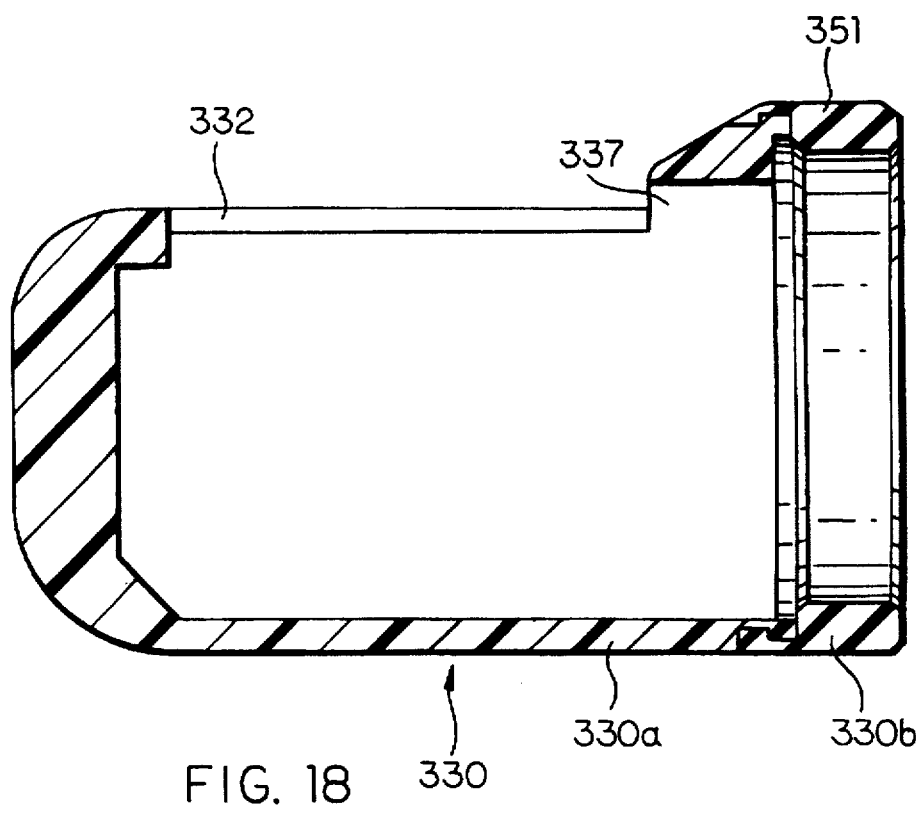

A third embodiment of the present invention which is applied to a side view type endoscope in which the end cover (end cap) is comprised of an easily deformable portion (deformation permitting portion) having a high resiliency and a deformation restricting portion having an extremely low resiliency will be discussed below with reference to FIGS. 16 through 18. In the third embodiment, the end cover has a nozzle function. In FIGS. 16 through 18, the elements corresponding to those in the second embodiment are designated with like reference numerals and no detailed explanation thereof will be given herein.

As can be seen in FIG. 16, the structure of the front end body 301 is basically identical to that of the front end body 201 in the second embodiment, except for the air supply passage 325, the water supply passage 326, the air supply pipe 323 and the water supply pipe 324, provided in the front end body 301 extend in parallel with the axis of the longitudinal axis of the endoscope without being inclined. The front end body 301 is provided with a flat surface portion 301a between the cover lens 215 and the open ends of the air supply passage 325 and the water supply passage 326.

The end cover 330 is similar in shape to the end cover 230 of the second embodiment with the following exception. Specifically, the substantial part of the end cap 230 of the second embodiment is constituted by the easily deformable portion, i.e., the resilient main body and the latter is supported by the deformation restricting portion; whereas, the substantial part of the end cap 330 of the third embodiment is constituted by the deformation restricting portion and the easily deformable portion is provided only on the part of the deformation restricting portion corresponding to the front end body. Specifically, the end cap 330 is comprised of the deformation restricting portion 330a having an extremely low resiliency and the easily deformable portion 330b having a high resiliency, as shown in FIGS. 16 and 18. The end cap 330 is also provided with a view window 204, an opening 332 corresponding to the cover lens 215, etc., and an air/water injection nozzle 337 opposed to the flat surface portion 301a of the front end body 301 when the end cap 330 is attached to the front end body 301. The easily deformable portion 330b provided on the rear portion of the end cap 330 is provided with an inner flange 351 which can be engaged in the peripheral groove 307 of the front end body 301, so that when the end cap 330 is attached to the front end body 301, no accidental detachment of the end cap from the front end body 301 occurs.

Similarly to the first embodiment applied to the front view type endoscope, the inner flange 451 in the third embodiment is elastically deformed (expanded) to be engaged with the front end body 301 upon attachment or detachment of the end cap 330, and hence, the end cap 330 can be easily attached to or detached from the front end body 301 of the endoscope. Furthermore, the deformation restricting portion 330a ensures that the original shape is basically maintained during the attachment or detachment of the end cap, and accordingly, no breakage of the end cap due to over deformation (i.e., beyond the elastic limit) takes place.

After the end cap 330 is removed from the front end body of the endoscope, the air supply pipe 223 and the water supply pipe 224 can be easily brushed through the exposed air supply passage 325 and water supply passage 326, as in the second embodiment. The nozzle 337 of the detached end cap 330 can be easily washed from either side.

The present invention is not limited to the illustrated embodiments, and can be applied, for example, to an oblique view type endoscope. Furthermore, the endoscope can be provided with a jet injection nozzle to inject the water in the forward direction, in addition to the air/water injection nozzle oriented toward the outer surface of the view window.

Although the invention has been described with reference to particular means, materials and embodiments, it is to be understood that the invention is not limited to the illustrated embodiments but to all equivalents within the scope of the following claims.

We claim:

1. An endoscope having an elongated insertion portion, comprising:
    a front end body provided on a front end of the elongated insertion portion; and,
    a detachable front end cap which alone covers said front end body said detachable front end cap having an easily deformable member having a relatively high resiliency and a deformation restricting member having a relatively low resiliency with respect to said easily deformable member;
    wherein said easily deformable member and said deformation restricting member are interconnected to form said front end cap.

2. An endoscope according to claim 1, wherein said front end body is provided, on the front end of the insertion portion, with a view window, and wherein said front end cap is provided with an opening corresponding to the view window, so that the view window can be exposed outside of said endoscope through the opening.

3. An endoscope according to claim 1, wherein said front end body is provided, on the side surface thereof, with a view window, and wherein said front end cap is provided with an opening corresponding to the view window, so that the view window can be exposed to the outside through the opening.

4. An endoscope in accordance with claim 1 wherein said easily deformable member and said deformation restricting member are provided with mating hook portions adapted to interconnect with each other to form said front end cap.

5. An endoscope having an elongated insertion portion, comprising:
    a front end body provided on a front end of the elongated insertion portion; and,
    a detachable front end cap which alone covers said front end body,
    wherein said front end cover is comprised of a cover portion which covers the front end body and an engaging portion which engages with the front end body, and,
    wherein said engaging portion is made of a relatively easily deformable member having a high resiliency, and said cover portion being made of a deformation restricting member having a relatively lower resiliency than the easily deformable members and wherein said engaging portion and said cover portion are interconnected to form said front end cover.

6. An endoscope according to claim 5, wherein said front end body is provided, on the front end of the insertion portion, with a view window, and wherein said front end cap is provided with an opening corresponding to the view window, so that the view window can be exposed to the outside through the opening.

7. An endoscope according to claim 6, wherein said front end body is provided on the front end portion thereof with an air supply passage and a water supply passage, and wherein said front end cap is integrally provided with a nozzle portion oriented toward the view window and connected to the air supply passage and the water supply passage when the front end cap is attached to the front end body.

8. An endoscope according to claim 7, wherein said front end body and said front end cap are both cylindrical.

9. An endoscope according to claim 7, wherein said front end cap is provided on the outer peripheral surface thereof with at least one engaging recess which can be engaged by a tool which is used to remove the front end cap from the front end body.

10. An endoscope according to claim 9, wherein said engaging portion is provided on the inner peripheral surface thereof with an engaging projection corresponding to the engaging recess and extending in the axial direction, said front end body being provided with an axially extending engaging groove in which the engaging projection of the engaging portion can be engaged when the front end cap is attached to the front end body.

11. An endoscope according to claim 5, wherein said front end body is provided, on the side surface thereof, with a view window, and wherein said front end cap is provided with an opening corresponding to the view window, so that the view window can be exposed to the outside through the opening.

12. An endoscope according to claim 11, wherein said front end body is provided with an air supply passage and a water supply passage, both opening toward the view window, and wherein said front end cap is integrally provided with a nozzle portion connected to the air supply passage and the water supply passage when the front end cap is attached to the front end body.

13. An endoscope in accordance with claim 5 wherein said easily deformable member and said deformation restricting member are provided with mating hook portions adapted to interconnect with each other to form said front end cap.

14. An endoscope having an elongated insertion portion to be inserted in a human body, comprising:

a front end body provided on a front end of the elongated insertion portion;

a detachable front end cap which is detachably attached to the front end body to cover the front end body; and, a view window which is provided on a side surface of the front end portion and is exposed to the exterior of said endoscope through the front end cap;

wherein said front end cover further comprises an easily deformable member having a high resiliency; and, a deformation restricting member having a lower resiliency than the easily deformable member, said easily deformable member being supported, at least at the portion thereof that engages with the front end body, by the deformation restricting members said front end cap being provided with at least one slit which enables said front end cap to elastically deform when the front end cap is attached to the front end body.

15. An endoscope according to claim 14, wherein said front end body is provided with an air supply passage and a water supply passage, both opening toward the view window, and wherein said front end cap is integrally provided with a nozzle portion connected to the air supply passage and the water supply passage when the front end cap is attached to the front end body.

16. An endoscope according to claim 14, wherein said front end cap and the deformation restricting member are cylindrical and wherein said at least one slit of said front end cap is provided on said deformation restricting member on a portion thereof corresponding to the engaging portion of the front end cap.

17. An endoscope having an elongated insertion portion; and, a detachable front end cap which alone covers said front end body, said front end cap having a deformable member and an undeformable member, wherein said deformable member and said undeformable member are interconnected to form said front end cap.

* * * * *